United States Patent [19]
Pommer et al.

[11] Patent Number: 5,882,718
[45] Date of Patent: Mar. 16, 1999

[54] METHOD FOR TREATING AN AQUEOUS PROTEIN SOLUTION TO KILL MICROORGANISMS THEREIN WITHOUT CAUSING COAGULATION AND COMPOSITION THEREOF

[75] Inventors: Klaus Pommer, Farum; Egon Christensen, Randers, both of Denmark

[73] Assignee: Novo Nordisk A/S, Bagsvaerd, Denmark

[21] Appl. No.: 809,540

[22] PCT Filed: Sep. 20, 1995

[86] PCT No.: PCT/DK95/00375

§ 371 Date: Mar. 6, 1997

§ 102(e) Date: Mar. 6, 1997

[87] PCT Pub. No.: WO96/08974

PCT Pub. Date: Mar. 28, 1996

[30] Foreign Application Priority Data

| Sep. 20, 1994 | [DK] | Denmark | 1081/94 |
| Sep. 27, 1994 | [DK] | Denmark | 1110/94 |
| Oct. 14, 1994 | [DK] | Denmark | 1187/94 |

[51] Int. Cl.⁶ .................................................. A23L 1/318
[52] U.S. Cl. ............................. 426/641; 426/44; 426/46; 426/56; 426/520; 426/634; 426/646
[58] Field of Search ...................... 426/641, 646, 426/634, 520, 46, 44, 56

[56] References Cited

U.S. PATENT DOCUMENTS 4,164,589  8/1979  Kadane et al. .......................... 426/281
5,232,723  8/1993  Bisson et al. .......................... 426/641

OTHER PUBLICATIONS

Olsen et al. Abstract, "Industrial Production of soya protein" Process Biochemistry, 14(7)6, 8, 10–11, 1979.

Dialog Info. Services File 51, Food Sci. & Tech. Abs., Dialog Accesion No. 00094710, FSTA Accession No. 75–03–s0329.

*Primary Examiner*—Helen Pratt
*Attorney, Agent, or Firm*—Steve T. Zelson; Cheryl H. Agris; Carol E. Rozek

[57] ABSTRACT

A method for treating an aqueous protein solution so as to kill microorganisms which may be present therein, but without causing coagulation, comprises either (1) mixing the solution with sufficient enzymatically produced protein hydrolysate (H1) to prevent coagulation of the mixture when the mixture is subsequently subjected to a heat treatment to kill microorganisms, and then subjecting the mixture to such a heat treatment, or (2) using one or more enzymes to hydrolyze protein in the aqueous protein solution to an extent sufficient to prevent coagulation of the resulting liquid hydrolysate (H2) when it is subsequently subjected to a heat treatment to kill microorganisms, and then subjecting the liquid hydrolysate (H2) to such a heat treatment. The use of aqueous protein solutions treated in this manner in the production of a foodstuff, such as a meat-based foodstuff, contributes very significantly to reducing any risk of contamination of the foodstuff by harmful microorganisms.

26 Claims, No Drawings

METHOD FOR TREATING AN AQUEOUS PROTEIN SOLUTION TO KILL MICROORGANISMS THEREIN WITHOUT CAUSING COAGULATION AND COMPOSITION THEREOF

CROSS-REFERENCE TO RELATED APPLICATIONS

This application is a 35 U.S.C. 371 national application of PCT/DK95/00375 filed Sep. 20, 1995 and claims priority under 35 U.S.C. 119 of Danish applications 1081/94, 1110/94 and 1187/94 filed Sep. 20, 1994, Sep. 27, 1994 and Oct. 14, 1994, the contents of which are fully incorporated herein by reference.

TECHNICAL FIELD OF THE INVENTION

The present invention provides, inter alia, a method for treating an aqueous protein solution, notably an aqueous protein solution for use in the production of a foodstuff, such as a meat-based foodstuff, so as to kill microorganisms, notably pathogenic microorganisms such as pathogenic bacteria, which may be present in the solution whilst avoiding coagulation of the proteinaceous component(s) of the solution. The invention further provides a method for producing a foodstuff, e.g. a meat-based foodstuff, in which is incorporated a treated aqueous protein solution produced in accordance with the latter method of the invention.

BACKGROUND OF THE INVENTION

In many countries it is common practise to process certain foodstuffs, particularly various types of meat or meat-based foodstuffs, by the addition thereto of proteinaceous solutions or extracts. The purpose of such treatment is not only to supplement the nutritional content of the product, but often also to modify its texture and/or consistency.

In the meat industry, a number of types of meat products, e.g. pork meat products such as ham, bacon and sirloin, are subjected to a process popularly known as "pumping", in which the natural meat juice—containing, inter alia, plasma proteins and possibly other soluble proteins—which exudes or is pressed from fresh meat on standing (e.g. when slabs or pieces of meat are stacked on top of one another) is reintroduced into the meat, typically by injection via a multiplicity of hollow needles (resembling hypodermic needles) or by more or less prolonged "tumbling" of the slabs or pieces of meat in a vessel containing the collected meat juice. Processes of these types have been employed routinely for many years.

In recent years there has been increasing awareness and concern in relation to the possibility of poultry and other types of meat being infected with, in particular, pathogenic microorganisms such as species of Salmonella or Listeria bacteria, with resultant risk of disease outbreak following human consumption of meat or meat-based foodstuffs infected in this manner. In this connection, there seems to be a considerable risk of meat juice—or indeed other proteinaceous media such as aqueous media containing vegetable protein(s)—becoming infected with undesirable microorganisms, notably pathogenic microorganisms, at some point during the process of collection and delivery for subsequent incorporation into the meat or other foodstuff. It has now been demonstrated in connection with the present invention (see the working examples provided herein) that this risk is very real, and the invention provides a simple, inexpensive and nutritionally very acceptable solution to the problem of ensuring the elimination of, e.g., pathogenic microorganisms from proteinaceous solutions immediately prior to the incorporation of such solutions in foodstuffs.

DESCRIPTION OF THE INVENTION

The present invention thus provides a method for treating an aqueous protein solution—in particular an aqueous protein solution for use in the production of a foodstuff—so as to kill microorganisms, e.g. pathogenic microorganisms, such as pathogenic bacteria, which may be present in the protein solution, without causing any significant coagulation of the proteinaceous component(s) of said solution, the method comprising the steps of either:

mixing the protein solution with an amount of an enzymatically produced protein hydrolysate (hereafter often denoted H1) which is sufficient to substantially prevent coagulation in the mixture when the mixture is subsequently subjected to a heat treatment to kill the microorganisms, and then subjecting the mixture to a heat treatment to kill the microorganisms; or subjecting the protein solution to hydrolysis using one or more enzymes so as to at least partly hydrolyze protein in the solution to an extent sufficient to substantially prevent coagulation of the resulting liquid hydrolysate (hereafter often denoted H2) when this hydrolysate is subsequently subjected to a heat treatment to kill the microorganisms, and then subjecting the hydrolysate H2 to a heat treatment to kill the microorganisms.

As will be apparent from the above, the method of the invention is well suited for the treatment of an aqueous protein solution so as to kill pathogenic microorganisms (i.e. disease-producing microorganisms, especially those capable of producing disease in humans and, possibly, animals) which may be present in the aqueous protein solution in question. Pathogenic microorganisms of particular relevance in the context of the invention include, for example, pathogenic bacteria such as species of Listeria (e.g. *L. monocytogenes*), Salmonella (e.g. *S. enteritidis* and *S. typhimurium*), Staphylococcus and Streptococcus. Another microorganism which should be mentioned in this respect is the strain of *Escherischia coli* known as *E. coli* 157.

As described and demonstrated in the following, simply heating a protein-containing aqueous solution such as meat juice to a temperature high enough to ensure killing of, e.g., pathogenic bacteria which may be present in the juice results in extensive coagulation (protein precipitation), rendering the heat-treated product essentially useless for incorporation in foodstuffs; moreover, dilution of, e.g., meat juice to reduce the protein concentration therein does not prevent coagulation taking place upon heating. In developing the above-described method according to the present invention, in which the protein solution is either mixed with an enzymatically produced protein hydrolysate (H1) (containing protein hydrolysis fragments in the form of peptides and/or amino acids) or is itself subjected to at least partial enzymatic hydrolysis so as to form peptides and/or amino acids, it was surprisingly found that a protein solution treated in this manner can be heated to kill harmful or otherwise undesirable microorganisms without causing coagulation, thus rendering the product obtained by the method well suited for incorporation into foodstuffs.

Since the method of the invention is primarily intended for application in the field of foodstuff preparation, it will be clear that the the aqueous protein solution employed will normally preferably contain protein of animal and/or vegetable origin, notably protein originating from animals or plants commonly employed in foodstuff preparation. Thus, for example, soluble proteins of animal meat origin, such as meat juice proteins from, e.g., pork, beef, mutton, venison, chicken, turkey, duck or goose, will in general be well suited for certain applications of the method of the invention, e.g. applications in which meat juice proteins are to be incorporated in corresponding meat-based foodstuffs. Likewise, soluble vegetable proteins from, e.g., soya or pea will generally be well suited for some applications of the method of the invention. However, soluble proteins from other sources, such as nutritionally acceptable soluble proteins of fungal (e.g. yeast) or bacterial origin, may also be of relevance in the context of the invention.

With respect to the enzymatically produced protein hydrolysate (H1) which may be employed in the method of the invention, a very suitable hydrolysate—particularly when the aqueous protein solution is, or comprises, an animal protein solution such as meat juice—is a hydrolysate prepared from animal protein, such as essentially insoluble animal protein in the form of so-called "greaves" (sometimes also called "graves"), which is proteinaceous material found in animal fat or tallow, and which forms a sediment on melting the fat. Greaves, for example pork greaves (i.e. greaves obtained from pork fat), are used, for example, in the manufacture of certain minced-meat foodstuffs, snack foods (in fried or roasted form, e.g. "cracklings") and dog food, and greaves per se are thus an acknowledged and approved source of supplementary nutritional protein for human and animal consumption.

Suitable animal protein hydrolysates (H1) may be prepared by hydrolysis of the animal protein in question, e.g. greaves, using one or more appropriate hydrolytic enzymes (i.e. hydrolases), preferably one or more proteases (peptidases). Likewise, when subjecting an aqueous protein solution to hydrolysis in accordance with the method of the invention (i.e. when forming an hydrolysate H2), it will be also be preferable to employ one or more proteases.

Protein hydrolysates (H1), e.g. animal protein hydrolysates (H1) such as greaves hydrolysates, for use in the context of the invention are preferably employed in liquid form, as prepared, but the use of dried (e.g. spray- or freeze-dried) protein hydrolysates (H1) which are either dissolved directly in the aqueous protein solution which is to be treated, or dissolved in some other suitable aqueous medium before being added to the aqueous protein solution in question, may also be appropriate in some instances.

In performing hydrolysis reactions in the context of the invention (i.e. in preparing a protein hydrolysate H1 for use in the method of the invention, or in subjecting the aqueous protein solution in question to hydrolysis to form a hydrolysate H2 in accordance with the method of the invention), it will frequently be advantageous—e.g. in the preparation of a greaves hydrolysate or a meat juice protein hydrolysate—that the initial protein content of the hydrolysis medium, calculated on the basis of protein dry matter, is in the range of 4–16 weight percent [% (w/w)], often preferably about 8–10% (w/w).

By way of example, wet pork greaves typically contain about 25–30% (w/w) of protein, and a suitable initial mixture for the preparation of a pork greaves hydrolysate useful in the context of the present invention will thus contain greaves and water in a weight ratio of about 1:2. Similarly, undiluted meat juice, e.g. pork meat juice, typically contains about 10–12% (w/w) of protein, and it may thus be appropriate to dilute the meat juice slightly to reduce the protein content thereof to about 8–10% (w/w) before carrying out the hydrolysis procedure.

With respect to the extent of protein hydrolysis which is desirable in hydrolysates H1 and H2 in the context of the present invention, a suitable Degree of Hydrolysis (DH) as defined herein (vide infra) will often be a DH in the range of 2–20%, often preferably about 6–10%. In the case, for example, of the preparation of a greaves hydrolysate or a meat juice protein hydrolysate, a DH of about 8% will typically be very suitable.

Proteases [i.e. enzymes classified under the Enzyme Classification number E.C. 3.4 in accordance with the Recommendations (1992) of the International Union of Biochemistry and Molecular Biology (IUBMB)] which are suitable for use in the context of the invention include proteases of bacterial, fungal, vegetable or animal origin. A wide variety of proteases are believed to be useful in the context of the invention, although preferred proteases will be those which result in protein hydrolysates (i.e. hydrolysates H1 or H2 as defined herein) with little or no bitter taste or other undesirable organoleptic properties. Proteases selected among those of the endopeptidase type appear to be well suited in the context of the present invention, and suitable examples thereof may be selected from those classified under the Enzyme Classification (E.C.) numbers:

3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin);

3.4.22 (i.e. so-called cysteine endopeptidases), including 3.4.22.2 (Papain), 3.4.22.3 (Ficain), 3.4.22.6 (Chymopapain), 3.4.22.7 (Asclepain), 3.4.22.14 (Actinidain), 3.4.22.30 (Caricain) and 3.4.22.31 (Ananain);

3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and 3.4.24 (i.e. so-called metalloendopeptidases), including 3.4.24.28 (Bacillolysin).

In connection with the use of one or more proteases in the performance of hydrolysis reactions in the context of the invention (i.e. in preparing a protein hydrolysate H1 for use in the method of the invention, or in subjecting the aqueous protein solution in question to hydrolysis to form a hydrolysate H2 in accordance with the method of the invention), the protease(s) is/are suitably added to the protein-containing hydrolysis medium in an amount [expressed herein in so-called Anson Units (AU; vide infra)] corresponding to 0.05–15 Anson Units per 100 grams of protein (as protein dry matter), such as 0.1–8 Anson Units per 100 grams of protein. In the case, for example, of the preparation of protein hydrolysates from greaves protein (e.g. from wet pork greaves, containing typically about 25–30 weight % of protein) or from meat juice proteins, an amount of protease (s) corresponding to about 1–1.2 AU/100 g protein is generally very suitable.

The Anson Unit (AU) scale for quantifying the proteolytic activity of a protease is based on a procedure in which denatured haemoglobin is digested with the protease. The undigested haemoglobin is precipitated with trichloroacetic acid (TCA), and the TCA-soluble product is determined using phenol reagent, which gives a blue colour with the amino acids tyrosine and tryptophan.

One AU is defined as the amount of enzyme which under standard conditions (25° C., pH 7.5, 10 minutes reaction time) digests haemoglobin at an initial rate such that an amount of TCA-soluble product giving the same colour intensity (with phenol reagent) as one milliequivalent of tyrosine is liberated per minute. A brochure ("AF 4/5") describing the analytical method in more detail is available from Novo Nordisk A/S, DK-2880 Bagsværd, Denmark, upon request.

Examples of well suited, readily commercially available proteases for use in the context of the invention include:

Protamex™ (from Novo Nordisk A/S, Bagsværd, Denmark; microgranulate of activity 1.5 AU per gram), which is a Bacillus protease complex that produces non-bitter protein hydrolysates; optimum pH is given as 5.5–7.5, and optimum temperature is given as 40°–60° C.

Alcalase™ Food Grade [from Novo Nordisk A/S; available as Alcalase 0.6 L and Alcalase 2.4 L (liquids) with activities of 0.6 and 2.4 AU per gram, respectively], which is produced from a selected strain of Bacillus licheniformis, and the main enzyme component of which is Subtilisin A (=Subtilisin Carlsberg; E.C. 3.4.21.62); optimum pH is given as 6.5–8.5, and optimum temperature is given as 55°–70° C.

Esperase™ Food Grade [E.C. 3.4.21.62; from Novo Nordisk A/S; available as Esperase 7.5 L (liquid) of activity 7.5 Kilo Novo Protease Units per gram, corresponding to approx. 2.2 AU per gram], which is produced from a selected strain of Bacillus lentus; optimum pH is given as 7.5–10.0, and optimum temperature is given as 55°–75° C.

Neutrase™ [E.C. 3.4.24.28; from Novo Nordisk A/S; available as Neutrase 0.5 L (liquid), Neutrase 1.5 MG (microgranulate) and Neutrase 4.5 BG (agglomerated powder) with activities of 0.5, 1.5 and 4.5 AU per gram, respectively], which is produced from a selected strain of Bacillus subtilis; optimum pH is given as 5.5–7.5, and optimum temperature is given as 45°–55° C.

The pH and temperature employed in performing hydrolysis reactions in the context of the invention (i.e. in preparing a protein hydrolysate H1 for use in the method of the invention, or in subjecting the aqueous protein solution in question to hydrolysis to form a hydrolysate H2 in accordance with the method of the invention) will be chosen on the basis, inter alia, of the optimum working pH and temperature characteristics of the enzyme or enzymes employed.

In general, when one or more proteases are employed in the hydrolysis reactions in question, a suitable pH during the hydrolysis reactions will be a pH in the range of 6–8.5, preferably 6–7.5, whilst the temperature will suitably be in the range of 40°–75° C., preferably 50°–60° C., e.g. about 55° C. These pH and temperature conditions appear to be very suitable in connection with the use, for example, of a wide variety of proteases of the endopeptidase type, e.g. the commercially available proteases mentioned above.

Hydrolysis reactions in the context of the invention may suitably be performed using a "pH-stat" technique, i.e. such that the pH during the hydrolysis reaction is kept essentially constant by the gradual addition of base (e.g. NaOH) in order to replenish hydroxide ions consumed during the enzyme-catalyzed hydrolysis of the protein(s) in question; a suitable pH in this connection will often be a pH of about 7–7.5. In the pH-stat approach, the pH of the hydrolysis reaction medium may, if desired, be monitored and adjusted manually, i.e. by measuring the pH regularly (e.g. by means of a pH meter) and adding an appropriate quantity of base (e.g. sodium hydroxide solution of suitable concentration). However, it will—particularly when carrying out hydrolysis reactions of the types in question on a large scale—clearly be preferable to employ automatic monitoring and adjustment of pH, and equipment for this purpose is well known and is available from a variety of commercial sources. The hydrolysis is allowed to proceed until the desired degree of hydrolysis (DH; vide infra) of the protein(s) in question is attained.

Alternatively, hydrolysis reactions in the context of the invention may often suitably be carried out without employing addition of base during the hydrolysis process. In this case, the initial pH of the hydrolysis medium will, if necessary, normally be adjusted to an appropriate value (e.g. often a value in the range of 7.5–8.5), after which the hydrolysis is allowed to proceed to an appropriate extent at the temperature of choice, with attendant gradual fall in the pH of the hydrolysis medium (e.g. often to a value of about 6–6.5).

Inactivation of an enzyme, such as a protease, employed in the context of the invention can often be achieved, for example, by lowering (e.g. temporarily) the pH of the medium and maintaining the lowered pH value for an appropriate length of time.

As already indicated to some extent, the above-described method according to the invention is particularly well suited for applications in which the foodstuff to be produced is a meat-based foodstuff. Meat-based foodstuffs may be broadly classified as either:

whole-meat foodstuffs, i.e. foodstuffs which predominantly consist of or contain relatively large cooked or uncooked pieces, chunks, lumps, slices, etc., of meat as cut from the slaughtered animal in question or of meat constituted of relatively small fragments or pieces of such meat which have been "glued" together (e.g. using gelatin or another suitable, approved proteinaceous "adhesive"); or minced-meat foodstuffs (i.e. foodstuffs comprising, as the meat component thereof, finely minced, ground or otherwise comminuted meat.

Meat-based foodstuffs which are of interest in the context of the present invention include smoked and/or boiled and/or cured (e.g. salt-cured) meat-based foodstuffs, i.e. smoked and/or boiled and/or cured whole-meat and minced-meat foodstuffs. Examples of whole-meat foodstuffs of interest include: smoked and/or boiled ham; bacon; smoked and/or boiled sirloin of pork or beef; smoked, cured saddle of pork; smoked and/or boiled, cured poultry meat (e.g. turkey, chicken, duck or goose meat); other types of smoked and/or boiled, cured fowl meat; and smoked and/or boiled rolled-meat sausage. Examples of minced-meat foodstuffs which are of interest include pork sausage, poultry meat sausage, beef sausage and beef hamburger.

In connection with the production of meat-based foodstuffs, it is preferred when the method of the invention is performed via hydrolysis of the aqueous protein solution in question that the protein solution is mixed with whole-meat trimmings and/or insoluble animal protein, e.g. greaves, before carrying out the hydrolysis; the resulting mixture is then subjected to the hydrolysis procedure (e.g. using one or more proteases) so as to form a hydrolysate (H2) containing at least partly hydrolysed protein originating from both the aqueous protein solution and from the added whole-meat trimmings and/or insoluble animal protein. As before, the hydrolysis is performed to an extent which is sufficient to substantially prevent coagulation of the resulting liquid hydrolysate (H2) when this hydrolysate is subsequently subjected to a heat treatment to kill microorganisms, e.g. pathogenic microorganisms, which may be present.

The considerations described above with respect to (i) the initial protein content in the hydrolysis medium/mixture, (ii) the initial enzyme:protein ratio in the hydrolysis medium/mixture, and (iii) the Degree of Hydrolysis (DH) of the hydrolysate (H2) also apply in relation to this latter embodiment of the method of the invention. Thus, for example, when whole-meat trimmings and/or greaves are added to the protein solution in question, the protein contribution from the protein content of the trimmings and/or greaves should be taken into account in establishing the hydrolysis conditions which are to be employed. In this connection it may be mentioned that whole-meat trimmings, which normally contain meat per se as well as fat and possibly some cartilage, gristle and/or bone, will often have a protein content of about 20%.

In the method of the invention it may, depending on the particular circumstances, be appropriate to remove any solids or other undissolved material which may be present in the liquid phase which is to be heat treated, notably any undissolved material (e.g. excess whole-meat trimmings and/or insoluble animal protein) present after the aqueous protein solution in question has been subjected to hydrolysis with one or more enzymes. This may be done before or after carrying out the heat-treatment step of the method. Suitable techniques herefor will normally be, e.g., centrifugation or filtration. Skimming or decantation may be suitable in some cases (e.g. for removal of a layer of fatty material).

When reference is made in the present specification and claims to the carrying out of a heat treatment of a mixture of an aqueous protein solution and a protein hydrolysate H1, or of a liquid hydrolysate H2, so as to kill microorganisms, it is to be understood that the heat treatment in question takes place at a sufficient temperature, and for a sufficient period of time, to cause killing of a microorganism among those in question to such an extent that testing of a sample of the resulting heat-treated mixture or hydrolysate, or of a sample of a foodstuff into which such a heat-treated mixture or hydrolysate has been incorporated, for the presence of the microorganism in question by means of a prescribed or recommended (e.g. by a national or regional regulatory or health authority) method for the detection thereof in foodstuffs gives a negative result.

Thus, for example, in the case of the Nordic countries, the so-called Nordic Committee on Food Analysis ("Nordisk Metodikkommité för Livsmedel"; in the following abbreviated as NMKL), Uppsala, Sweden, publishes prescribed standard methods for the detection of various microorganisms, including pathogenic microorganisms such as species of Listeria or Salmonella bacteria, in foods (e.g. meat and cheese products). These NMKL methods are published, e.g., in Swedish and English, and in the context of the present invention the NMKL method for detection of a particular microorganism (for example a pathogenic microorganism among those of relevance mentioned above, e.g. a Listeria species such as *Listeria monocytogenes*) or group of microorganisms (e.g. various Salmonella species) constitutes a suitable method for determining whether satisfactory killing (as defined herein) of the particular microorganism(s) in question has taken place.

With regard to the temperature and duration of heating which should be employed in the heat-treatment step of the method of the invention in order to achieve satisfactory killing of the microorganism(s) of interest, it is difficult to give any very precise general guidelines herefor, and the conditions to be chosen will depend to a large extent on the exact nature of the microorganisms) to be killed. However, ignoring any other considerations it will be clear that, in general, the use of relatively high temperatures in the heat-treatment step will make it possible to employ relatively short treatment times.

For many microorganisms (e.g. numerous pathogenic microorganisms, such as pathogenic bacteria) of relevance in the context of the invention, the required duration of the heat treatment when employing temperatures of about 70° C. or above will—depending, inter alia, on the actual content of the microorganism(s) of interest in the protein solution/hydrolysate H1 mixture, or the liquid hydrolysate H2, which is to be subjected to heat treatment—be at the most a few minutes, e.g. at the most about 10 minutes, often at most about 5 minutes and in many cases at most about 1 or 2 minutes.

Thus, by way of example, experiments performed in connection with the present invention indicate (vide infra) that a heat treatment involving heating to a temperature of about 70° C. (or above) causes rapid killing (as defined herein) of various microorganisms, e.g. pathogenic microorganisms such as species of Salmonella or Listeria bacteria (which are among microorganisms of particular importance in the context of the invention).

In connection with embodiments of the method of the invention in which the aqueous protein solution in question is mixed with a protein hydrolysate (H1), it will be clear that the value of the most appropriate mixing ratio will depend on, inter alia, the nature and concentration of the protein solution, and the nature, concentration and Degree of Hydrolysis (DH) of the hydrolysate H1; it is thus difficult to give general guidelines concerning the mixing ratio to be employed. When the aqueous protein solution is (undiluted) pork meat juice, and the protein hydrolysate H1 is a pork greaves hydrolysate prepared in accordance with a working example given herein (see Example 1), a suitable ratio of meat juice to greaves hydrolysate is about 20:80 by weight; this ratio permits heating, if desired, to a temperature of about 80° C. or more, i.e. to a temperature considerably in excess of the above-mentioned temperature of about 70° C. If appropriate, however, a meat juice:greaves hydrolysate ratio lower than about 20:80 by weight (such as, e.g., 10:90 or 5:95 by weight), i.e. corresponding to a lower meat juice content in the mixture, may be employed.

The present invention also relates to a heat-treated mixture of protein solution and hydrolysate H1, or a heat-treated hydrolysate H2, obtainable by a method of the invention as described above.

A further aspect of the invention provides a method for producing a foodstuff (such as a meat-based foodstuff) in which is incorporated an aqueous solution comprising unhydrolysed and/or hydrolysed soluble protein, and preventing contamination of the foodstuff by microorganisms, particularly pathogenic microorganisms, as a direct result of this incorporation. This method comprises adding to one or more ingredients (e.g. the meat in the case of a meat-based foodstuff) forming the basis of the foodstuff a heat-treated mixture of a protein solution and a hydrolysate H1, or a heat-treated liquid hydrolysate H2, according to the invention, or prepared according to the first-described method of the invention.

In this connection, a still further aspect of the invention relates to a foodstuff (such as a meat-based foodstuff) producible by the latter method of the invention.

Meat-based foodstuffs which may suitably be prepared using the latter method of the invention include the whole-meat and minced-meat foodstuffs already mentioned above. In the case of whole-meat foodstuffs, the addition of the heat-treated mixture of protein solution and hydrolysate H1, or of the heat-treated liquid hydrolysate H2, may suitably take place either by needle injection thereof into the meat or by "tumbling" (i.e. rotating/stirring) the meat in the heat-treated protein solution/hydrolysate H1 mixture or the heat-treated liquid hydrolysate H2. The latter techniques of injection and tumbling, as well as the associated apparatus employed therefor, are well known per se and widely used in the meat industry.

In the case of minced-meat foodstuffs, the addition of the heat-treated mixture of protein solution and hydrolysate H1, or of the heat-treated liquid hydrolysate H2, may suitably be achieved by a procedure in which it is mixed with the meat and, if appropriate, other ingredients of the final minced-meat foodstuff. This mixing may suitably be achieved by exploiting the vigorous mixing effect associated with comminution of the meat, e.g. by mincing, grinding or otherwise comminuting the meat in the presence of the liquid phase in question.

Another aspect of the invention relates to the use of a heat-treated mixture of an aqueous protein solution and a protein hydrolysate H1, or of a heat-treated liquid hydrolysate H2, according to the invention, or produced according to a method of the invention, in the production of a foodstuff (such as a whole-meat or minced-meat foodstuff, examples of which have already been mentioned above).

It will be clear that those aspects of the invention which relate to the production of a foodstuff are particularly relevant when the product foodstuff in question is to be free of pathogenic microorganisms, i.e. a foodstuff in which the pathogenic microorganisms) in question cannot be detected on the basis of a prescribed or recommended detection method therefor as described above.

The invention is further described and illustrated by means of the working examples given below.

The °Brix scale referred to in Example 1, and employed here as a measure of the "dissolved dry matter" content of aqueous hydrolysate phases, is such that a solution with n °Brix has a density at 20° C. equal to that of an n% (w/w) sucrose solution in water at the same temperature. The determination of °Brix in Example 1 was made using a refractometer which was pre-calibrated to enable direct conversion of measured refractive index values at 20° C. to °Brix values (assuming a 1:1 correlation between the refractive index of liquid phase to be examined and the refractive index of a sucrose solution having the same density as the liquid phase in question). Tabulated values of the refractive index of sucrose solutions as a function of weight percentage [% (w/w)] of sucrose therein (at 20° C.) are given, for example, in R. C. Weast (editor), *Handbook of Chemistry and Physics*, 51st edition (1970–1971), The Chemical Rubber Co., Ohio, p. E-232.

EXAMPLE 1
Preparation of Greaves Hydrolysate 1,000 kg wet pork greaves were mixed with 2,000 kg of water and wet milled using a Fryma mill equipped with the toothed colloid mill head. The pH was adjusted to 7.5 with 5N NaOH, and the temperature of the mixture was adjusted to 55° C.

1.67 kg of Protamex™ (Novo Nordisk A/S; activity 1.5 Anson Units per gram) was added. The enzymatic hydrolysis was carried out as a pH-stat hydrolysis, the pH being held constant at 7.5 during the hydrolysis by gradual, continuous addition of NaOH. The hydrolysis was performed until a total base consumption of 25.0 liters of 5.0N NaOH. This corresponds to a Degree of Hydrolysis (DH) of approximately 8%, as calculated according to J. Adler-Nissen, *Enzymic Hydrolysis of Food Proteins*, 1st edition, Elsevier Applied Science Publishers, 1986, p 122; thus:

$$DH = B \times N_b \times (1/\alpha) \times (1/MP) \times (1/h_{tot}) \times 100\%$$

Where:
B=base consumption in ml
$N_b$=normality (equivalents/liter) of the base
5α=average degree of dissociation of the α-NH groups MP=mass of protein in g
$h_{tot}$=total number of peptide bonds (mequiv./g protein) in the protein substrate After the hydrolysis, the enzymes were inactivated by reducing the pH to 4.0 by addition of 30% (w/w) hydrochloric acid and maintaining the temperature of the mixture at 55° C. for 30 minutes. The pH was then readjusted to 6.5 by addition of 5.0N NaOH, and the temperature of the mixture was then increased to 80° C. before separating insoluble components as follows:

Insoluble proteinaceous material (sludge) was separated from the hydrolysate using a self-ejecting centrifuge (Westfalia SC 35 separator operating at a throughput of 1,000 l/h). Fat was separated from the aqueous phase using a Westfalia SB 7 separator operating at a throughput of 180–200 l/h.

The proteinaceous sludge was washed once with an equal volume of water, and the washings were then centrifuged as before. The resulting centrifugate was then mixed with the bulk liquid (aqueous) phase obtained after the initial separation of proteinaceous sludge and fat (vide supra), and the combined liquid phase was concentrated using a Niro Atomizer falling-film evaporator to a dissolved dry matter content of 48°Brix. Salt was then added to give a salt content corresponding to 33% of the °Brix dissolved dry matter content in order to prevent microbial growth in the product.

The composition by weight of the final product (greaves hydrolysate) was as follows:

water: 51%
protein: 33%
fat: 1%
salt: 15%

The water content was determined by weighing a sample before and after heating in a oven at 105° C. for 24 hours. The protein content (which includes the content of peptides and any amino acids present) was determined by the standard Kjeldahl method, multiplying the calculated % nitrogen by a Kjeldahl factor of 6.25. Fat was determined by Soxhlet extraction using trichloroethane or petroleum ether as extractant. Salt was determined by Mohr titration (see, e.g., J. S. Fritz and G. H. Schenk, *Quantitative Analytical Chemistry*, 2nd edition, Allyn and Bacon, Boston, 1971, pp. 203–204).

EXAMPLE 2
Coagulation Tendency of Mixtures of Meat Juice and Greaves Hydrolysate Upon Heating As already indicated, when meat juice is heated to temperatures above about 50°–55° C. it generally coagulates, and it is thus not possible to inject or tumble meat juice heated in this manner into meat. Even if meat juice is diluted very considerably (such as about 5-fold) using an appropriate aqueous medium, e.g. a salt solution, coagulation still occurs on heating to about 50°–55° C. However, it has now very surprisingly been found that it is possible to subject a mixture of meat juice and a protein hydrolysate to heat treatment without the occurrence of significant coagulation. The experiments described here were performed in order to establish more precisely the ratio of meat juice to hydrolysate (in this case a greaves hydrolysate) at which heat treatment could take place without giving rise to significant coagulation (or other form of precipation).

Liquid greaves hydrolysate (prepared as in Example 1) was mixed with pork sirloin meat juice in different weight ratios, and the various mixtures (100 ml of each) were then heated with magnetic stirring. Each mixture was observed during heating, and a mixture was judged to be acceptably stable in the context of the present invention if it could be heated to a temperature of 60° C. without significant coagulation or precipitation occurring. The results obtained are summarized in the table below:

| Hydrolysate, % (w/w) | Meat juice, % (w/w) | Result |
| --- | --- | --- |
| 0 | 100 | unstable |
| 50 | 50 | unstable |
| 75 | 25 | slightly unstable |
| 80 | 20 | stable |

A mixture containing 80% (w/w) hydrolysate and 20% (w/w) meat juice remained stable when heated to temperatures of 70° C. or above (e.g. to about 80° C.), at which temperatures pathogenic microorganisms of relevance in the context of the invention (e.g. bacteria of the genus Salmonella or Listeria) are rapidly killed (as defined herein). Unlike untreated meat juice, which coagulates at a temperature well below 70° C. (vide supra), such a mixture can thus be heat-treated to kill undesirable microorganisms and then introduced into whole-meat foodstuffs (e.g. by "pumping" by means of needle injection into the meat or by tumbling the meat in the mixture) or incorporated into minced-meat foodstuffs (e.g. by simply mixing the sterilized meat juice/hydrolysate mixture with meat—and possibly other ingredients of the final minced-meat foodstuff—and then mincing, grinding and/or otherwise comminuting the whole). A mixture containing 80% (w/w) hydrolysate and 20% (w/w) meat juice has a meat juice protein content of about 8–10% by weight of the total protein content (total protein content being defined as for the greaves hydrolysate prepared in Example 1).

EXAMPLE 3

Introduction ("pumping") of (a) Untreated Meat Juice and (b) Heat-treated Meat Juice/Hydrolysate Mixture Into Meat; Microbial Quality of the Resulting "Pumped" Meat Meat juice from pork sirloins and from ham, respectively, were collected separately and each divided into two portions. One portion of each type of meat juice was introduced into the corresponding meat (i.e. sirloin meat juice to sirloin, and ham meat juice to ham) by standard needle injection.

The second portion of each type of meat juice was mixed with pork greaves hydrolysate (prepared as described in Example 1) in a weight ratio (meat juice:hydrolysate) of 20:80. Both mixtures were heated to 70° C. and then cooled to 5° C. No significant coagulation of the meat juice protein in the mixtures was observed, and it was therefore possible to introduce each mixture into the corresponding meat by means of standard needle injection.

The two "pumped" pork sirloin samples were smoked and heat-treated in the smoking chamber. During the process, the temperature at the surface of the meat reached 65° C. and the temperature at the centre reached 40°–43° C. The samples were cooled to about 5° C. before slicing.

The two "pumped" ham samples were simply cooled to about 5° C. before slicing.

The centre region of slices taken from the centres of the four samples were tested with respect to microbial quality (content of *Listeria monocytogenes*) according to NMKL method No. 136 (1990), using 25 gram portions of the product in each case. The results were as follows:

Test for *Listeria monocytogenes*:

| | |
| --- | --- |
| Smoked sirloin + heat-treated meat juice/hydrolysate: | negative |
| Smoked sirloin + untreated meat juice: | positive |
| Raw ham + heat-treated meat juice/hydrolysate: | negative |
| Raw ham + untreated meat juice: | positive |

Some very important conclusions can be drawn on the basis of the latter results:

Thus, for example, firstly, and very surprisingly, the "traditional" process of smoking and heat-treating meat (e.g. pork) which has been pumped with untreated meat juice does not ensure the killing of a pathogenic bacteria originating from the meat juice employed in the "pumping" process. It should be noted in this respect that the meat juice (from pork sirloin and from ham) used in the experiments described in this example had not been deliberately inoculated in any way with *L. monocytogenes*, and the occurrence of this pathogenic organism in whole meat which had been "pumped" with untreated meat juice must therefore be the result of contamination of the meat juice prior to carrying out the "pumping" process.

Secondly, it is apparent that the *L. monocytogenes* originating from untreated meat juice from both types of meat is killed (as defined herein) satisfactorily by the heat treatment carried out on the meat juice/greaves hydrolysate mixture. The process of the invention, embodied in the present example, thus makes a very important contribution to eliminating the risk of infection of "pumped" meat products by harmful microorganisms.

It may also be mentioned here that some similar experiments carried out using untreated meat juice infected with Salmonella bacteria [and employing NMKL method No. 71 (1991) for detection of Salmonella] have produced results analogous to those described above for Listeria, thereby further confirming the above general conclusions concerning the effectiveness of the process of the invention.

We claim:

1. A method for treating an aqueous protein solution for use in the production of a foodstuff so as to kill microorganisms which may be present in said protein solution substantially without causing coagulation of the proteinaceous component(s) of said solution, the method comprising the steps of:

either:
 mixing said solution with an amount of an enzymatically produced protein hydrolysate (H1) sufficient to substantially prevent coagulation in the mixture when said mixture is subsequently subjected to a heat treatment so as to kill said microorganisms, and
 subjecting said mixture to a heat treatment so as to kill said microorganisms; or:
 subjecting said solution to hydrolysis using one or more enzymes so as to at least partly hydrolyze protein in said solution to an extent sufficient to substantially prevent coagulation of the resulting liquid hydrolysate (H2) when said hydrolysate (H2) is subsequently subjected to a heat treatment to kill said microorganisms, and
 subjecting said liquid hydrolysate (H2) to a heat treatment to kill said microorganisms.

2. The method according to claim 1, wherein said microorganisms comprise pathogenic microorganisms.

3. The method according to claim 1, wherein said aqueous protein solution comprises protein of animal and/or vegetable origin.

4. The method according to claim 1, wherein said aqueous protein solution comprises meat juice proteins.

5. The method according to claim 1, wherein said aqueous protein solution comprises soya and/or pea proteins.

6. The method according to claim 1, wherein said hydrolysate (H1) is an animal protein hydrolysate produced by hydrolysis of animal protein using one or more proteases.

7. The method according to claim 6, wherein said one or more proteases are proteases of bacterial, fungal, vegetable or animal origin.

8. The method according to claim 7, wherein said one or more proteases comprise a protease selected from the group consisting of serine endopeptidases (E.C. 3.4.21), cysteine endopeptidases (E.C. 3.4.22), aspartic endopeptidases (E.C. 3.4.23) and metalloendopeptidases (3.4.24).

9. The method according to claim 6, wherein said hydrolysate (H1) is a greaves hydrolysate.

10. The method according to claim 1, wherein said one or more enzymes comprise one or more proteases.

11. The method according to claim 1, wherein said foodstuff is a meat-based foodstuff.

12. The method according to claim 11, wherein said meat-based foodstuff is selected from the group consisting of whole-meat foodstuffs and minced-meat foodstuffs.

13. The method according to claim 11, the method further comprising the step of mixing said aqueous protein solution with whole-meat trimmings and/or insoluble animal protein, whereafter the mixture is subjected to said hydrolysis using one or more proteases so as to at least partly hydrolyze protein in said solution and in said whole-meat trimmings and/or insoluble animal protein to an extent sufficient to substantially prevent coagulation of the resulting liquid hydrolysate (H2) when said hydrolysate (H2) is subsequently subjected to a heat treatment to kill said microorganisms.

14. The method according to claim 13, wherein said insoluble animal protein is added in the form of greaves.

15. The method according to claim 1, further comprising the step of removing solids present in said hydrolysate (H2) before and/or after heat treatment thereof.

16. The method according to claim 1, wherein said heat treatment of said mixture or said hydrolysate (H2) comprises heating said mixture or said hydrolysate (H2) to a temperature of at least about 70° C.

17. The method according to claim 1, wherein said aqueous protein solution is pork meat juice and said protein hydrolysate (H1) is a pork greaves hydrolysate with a protein content (as defined herein) of about 30%, said mixing taking place in a meat juice:hydrolysate ratio of at most about 20:80 by weight.

18. A heat-treated protein solution/hydrolysate (H1) mixture or heat-treated liquid hydrolysate (H2) prepared according to claim 1.

19. A method for producing a meat-based foodstuff in which is incorporated an aqueous solution comprising unhydrolysed and/or hydrolysed soluble protein, and preventing contamination of the meat-based foodstuff by pathogenic microorganisms as a direct result of said incorporation, the method comprising adding to the meat forming the basis of said meat-based foodstuff a heat-treated protein solution/hydrolysate (H1) mixture or heat-treated liquid hydrolysate H2 prepared according to claim 11.

20. The method according to claim 19, wherein said meat-based foodstuff is selected from the group consisting of whole-meat foodstuffs and minced-meat foodstuffs.

21. The method according to claim 19, wherein said meat-based foodstuff is a whole-meat foodstuff selected from the group consisting of: smoked and/or boiled ham; bacon; smoked and/or boiled sirloin of beef; smoked and/or boiled sirloin of pork; smoked, cured saddle of pork; smoked and/or boiled, cured poultry meat; and rolled-meat sausage.

22. The method according to claim 19, wherein said meat-based foodstuff is a minced-meat foodstuff selected from the group consisting of pork sausage, beef sausage and beef hamburger.

23. The method according to claim 19, wherein said meat-based foodstuff is a whole-meat foodstuff, and wherein said addition of said heat-treated protein solution/hydrolysate (H1) mixture or heat-treated liquid hydrolysate (H2) takes place by needle injection thereof into said meat.

24. The method according to claim 19, wherein said meat-based foodstuff is a whole-meat foodstuff, and wherein said addition of said heat-treated protein solution/hydrolysate (H1) mixture or heat-treated liquid hydrolysate (H2) takes place by tumbling of said meat in said heat-treated protein solution/hydrolysate (H1) mixture or heat-treated liquid hydrolysate (H2).

25. The method according to claim 19, wherein said meat-based foodstuff is a minced-meat foodstuff, and wherein said addition of said heat-treated protein solution/hydrolysate (H1) mixture or heat-treated liquid hydrolysate (H2) comprises mixing thereof with said meat and, optionally, other ingredients of said minced-meat foodstuff, said mixing optionally taking place substantially simultaneously with comminution of said meat.

26. A meat-based foodstuff produced by a method according to claim 19.

* * * * *